(12) United States Patent
Fischer et al.

(10) Patent No.: US 7,214,701 B2
(45) Date of Patent: May 8, 2007

(54) ACTIVE SUBSTANCE COMBINATIONS HAVING INSECTICIDAL AND ACARICDAL PROPERTIES

(75) Inventors: Reiner Fischer, Monheim (DE); Christoph Erdelen, Leichlingen (DE)

(73) Assignee: Bayer CropScience AG, Monheim (DE)

( * ) Notice: Subject to any disclaimer, the term of this patent is extended or adjusted under 35 U.S.C. 154(b) by 56 days.

(21) Appl. No.: 10/876,829

(22) Filed: Jun. 25, 2004

(65) Prior Publication Data

US 2004/0235934 A1 Nov. 25, 2004

Related U.S. Application Data

(62) Division of application No. 10/276,579, filed as application No. PCT/EP01/05139 on May 7, 2001, now Pat. No. 6,864,276.

(30) Foreign Application Priority Data

May 19, 2000 (DE) ................. 100 24 934

(51) Int. Cl.
*A01N 43/02* (2006.01)
*A01N 43/34* (2006.01)
*A01N 43/36* (2006.01)
*A01N 43/38* (2006.01)
*A01N 43/40* (2006.01)
*A01N 43/42* (2006.01)
*A01N 43/48* (2006.01)
*A01N 43/72* (2006.01)
*A01N 43/84* (2006.01)
*A01N 57/00* (2006.01)

(52) U.S. Cl. .................... 514/409; 514/79; 514/80; 514/83; 514/84; 514/85; 514/89; 514/91; 514/95; 514/210.01; 514/210.19; 514/211.01; 514/211.15; 514/212.01; 514/218; 514/222.2; 514/228.8; 514/229.2; 514/229.5; 514/230.8; 514/231.2; 514/231.5; 514/232.8; 514/233.2; 514/233.5; 514/235.8; 514/236.8; 514/237.2; 514/237.5; 514/237.8; 514/238.8; 514/239.5; 514/241; 514/245; 514/247; 514/277; 514/278; 514/279; 514/299; 514/315; 514/332; 514/336; 514/337; 514/338; 514/339; 514/340; 514/341; 514/342; 514/343; 514/345; 514/352; 514/359; 514/360; 514/361; 514/365; 514/372; 514/374; 514/378; 514/381; 514/383; 514/385; 514/403; 514/407; 514/408; 514/410; 514/411; 514/412; 514/413; 514/414; 514/415; 514/416; 514/417; 514/418; 514/419; 514/420; 514/421; 514/422; 514/423; 514/424; 514/425; 514/426; 514/427; 514/428; 514/429; 514/430; 514/431; 514/432; 514/438; 514/449; 514/450; 514/451; 514/459; 514/461; 514/471; 514/475

(58) Field of Classification Search ............ 514/229.2, 514/245, 365, 409, 423, 471, 79–80, 83–85, 514/89, 91, 95, 210.01, 210.19, 211.01, 211.15, 514/212.01, 218, 222.2, 228.8, 229.5, 230.8, 514/231.2, 231.5, 232.8, 233.2, 233.5, 235.8, 514/236.8, 237.2, 237.5, 237.8, 238.8, 239.5, 514/241, 247, 277–279, 299, 315, 332, 336–345, 514/352, 354, 357–361, 372, 374, 378, 381, 514/383; 514/385, 403, 408–429, 430, 431, 514/432, 438, 449–451, 459, 461, 475
See application file for complete search history.

(56) References Cited

U.S. PATENT DOCUMENTS

| | | | |
|---|---|---|---|
| 3,364,177 A | 1/1968 | Bremmer | 260/47 |
| 4,053,634 A | 10/1977 | Bellina et al. | 424/312 |
| 4,055,661 A | 10/1977 | Bellina et al. | 424/311 |
| 4,070,481 A | 1/1978 | Bellina et al. | 424/311 |
| 4,082,848 A | 4/1978 | Bellina et al. | 424/273 R |
| 4,115,584 A | 9/1978 | Bellina et al. | 424/301 |
| 4,143,157 A | 3/1979 | Bellina et al. | 424/314 |
| 4,148,918 A | 4/1979 | Bellina et al. | 424/314 |
| 4,531,002 A | 7/1985 | Harris | 544/54 |
| 4,590,272 A | 5/1986 | Shiokawa et al. | 544/335 |
| 4,606,862 A | 8/1986 | Harris | 260/402.5 |
| 4,647,570 A | 3/1987 | Shiokawa et al. | 514/341 |

(Continued)

FOREIGN PATENT DOCUMENTS

CA 2052731 4/1992

(Continued)

OTHER PUBLICATIONS

Chemical Abstracts 130:338086 (1999).*

(Continued)

*Primary Examiner*—John Pak
(74) *Attorney, Agent, or Firm*—Richard E. L. Henderson

(57) ABSTRACT

The invention relates to insecticidal mixtures for protecting plants against attack by pests comprising
(a) compounds of the formula (I)

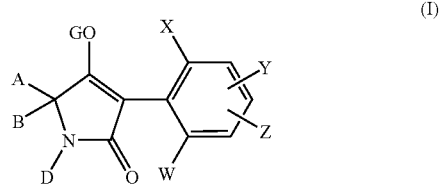

in which W, X, Y, Z, A, B, D and G are each as defined in the disclosure, and
(b) specified agonists or antagonists of nicotinic acetylcholine receptors.3340

6 Claims, No Drawings

U.S. PATENT DOCUMENTS

| | | |
|---|---|---|
| 4,678,795 A | 7/1987 | Shiokawa et al. .......... 514/341 |
| 4,680,294 A | 7/1987 | Shiokawa et al. .......... 514/256 |
| 4,687,845 A | 8/1987 | Hollowood et al. .......... 544/54 |
| 4,742,060 A | 5/1988 | Shiokawa et al. .......... 514/252 |
| 4,772,620 A | 9/1988 | Shiokawa et al. .......... 514/341 |
| 4,774,247 A | 9/1988 | Shiokawa et al. .......... 514/256 |
| 4,803,277 A | 2/1989 | Shiokawa et al. .......... 514/332 |
| 4,806,553 A | 2/1989 | Shiokawa et al. .......... 514/332 |
| 4,812,454 A | 3/1989 | Shiokawa et al. .......... 514/256 |
| 4,812,571 A | 3/1989 | Shiokawa et al. .......... 546/296 |
| 4,843,068 A | 6/1989 | Hamaguchi et al. .......... 514/63 |
| 4,845,106 A | 7/1989 | Shiokawa et al. .......... 514/342 |
| 4,849,432 A | 7/1989 | Shiokawa et al. .......... 514/341 |
| 4,882,344 A | 11/1989 | Shiokawa et al. .......... 514/342 |
| 4,914,113 A | 4/1990 | Shiokawa et al. .......... 514/333 |
| 4,918,086 A | 4/1990 | Gsell .......... 514/351 |
| 4,918,088 A | 4/1990 | Gsell .......... 514/357 |
| 4,948,798 A | 8/1990 | Gsell .......... 514/275 |
| 4,962,126 A | 10/1990 | Drabek .......... 514/587 |
| 4,963,572 A | 10/1990 | Gsell .......... 514/357 |
| 4,963,574 A | 10/1990 | Bachmann et al. .......... 514/357 |
| 4,988,712 A | 1/1991 | Shiokawa et al. .......... 514/340 |
| 5,001,138 A | 3/1991 | Shiokawa et al. .......... 514/342 |
| 5,010,098 A | 4/1991 | Brown et al. .......... 514/426 |
| 5,032,589 A | 7/1991 | Shiokawa et al. .......... 514/245 |
| 5,034,404 A | 7/1991 | Uneme et al. .......... 514/365 |
| 5,034,524 A | 7/1991 | Shiokawa et al. .......... 544/524 |
| 5,039,686 A | 8/1991 | Davies et al. .......... 514/341 |
| 5,049,571 A | 9/1991 | Gsell .......... 514/345 |
| 5,051,434 A | 9/1991 | Kozo et al. .......... 514/357 |
| 5,063,236 A | 11/1991 | Gsell .......... 514/318 |
| 5,066,808 A | 11/1991 | Shiokawa et al. .......... 514/231.5 |
| 5,084,467 A | 1/1992 | Shiokawa et al. .......... 514/357 |
| 5,166,164 A | 11/1992 | Nanjo et al. .......... 514/357 |
| 5,175,301 A | 12/1992 | Minamida et al. .......... 546/272 |
| 5,192,778 A | 3/1993 | Kodaka et al. .......... 514/341 |
| 5,204,359 A | 4/1993 | Shiokawa et al. .......... 514/332 |
| 5,204,360 A | 4/1993 | Shiokawa et al. .......... 514/342 |
| 5,214,152 A | 5/1993 | Minamida et al. .......... 548/181 |
| 5,238,949 A | 8/1993 | Shiokawa et al. .......... 514/327 |
| 5,256,679 A | 10/1993 | Minamida et al. .......... 514/357 |
| 5,258,527 A | 11/1993 | Krauskopf et al. .......... 548/543 |
| 5,264,584 A | 11/1993 | Kodaka et al. .......... 548/332.5 |
| 5,280,123 A | 1/1994 | Nanjo et al. .......... 548/111 |
| 5,298,507 A | 3/1994 | Shiokawa et al. .......... 514/256 |
| 5,304,566 A | 4/1994 | Ishimitsu et al. .......... 514/357 |
| 5,310,938 A | 5/1994 | Brown et al. .......... 548/557 |
| 5,367,093 A | 11/1994 | Dekeyser et al. .......... 560/27 |
| 5,384,324 A | 1/1995 | Shiokawa et al. .......... 514/365 |
| 5,405,961 A | 4/1995 | Nanjo et al. .......... 544/243 |
| 5,428,032 A | 6/1995 | Shiokawa et al. .......... 514/226.8 |
| 5,434,181 A | 7/1995 | Kodaka et al. .......... 514/471 |
| 5,438,123 A | 8/1995 | Dekeyser et al. .......... 534/885 |
| 5,455,263 A | 10/1995 | Doscher et al. .......... 514/422 |
| 5,461,167 A | 10/1995 | Shiokawa et al. .......... 548/202 |
| 5,462,913 A | 10/1995 | Fischer et al. .......... 504/138 |
| 5,478,855 A | 12/1995 | Suzuki et al. .......... 514/374 |
| 5,489,603 A | 2/1996 | Uneme et al. .......... 514/365 |
| 5,504,057 A | 4/1996 | Fischer et al. .......... 504/283 |
| 5,532,365 A | 7/1996 | Kodaka et al. .......... 544/212 |
| 5,536,746 A | 7/1996 | Dekeyser et al. .......... 514/468 |
| 5,567,671 A | 10/1996 | Fischer et al. .......... 504/283 |
| 5,580,889 A | 12/1996 | Shiokawa et al. .......... 514/343 |
| 5,589,469 A | 12/1996 | Fischer et al. .......... 514/91 |
| 5,602,078 A | 2/1997 | Fischer et al. .......... 504/283 |
| 5,612,358 A | 3/1997 | Ishimitsu et al. .......... 514/357 |
| 5,614,527 A | 3/1997 | Kinoshita et al. .......... 514/256 |
| 5,616,536 A | 4/1997 | Fischer et al. .......... 504/225 |
| 5,622,917 A | 4/1997 | Fischer et al. .......... 504/283 |
| 5,633,375 A | 5/1997 | Uneme et al. .......... 544/336 |
| 5,677,449 A | 10/1997 | Fischer et al. .......... 544/165 |
| 5,696,256 A | 12/1997 | Kando et al. .......... 540/463 |
| 5,719,146 A | 2/1998 | Shiokawa et al. .......... 514/229.2 |
| RE35,811 E | 5/1998 | Shiokawa et al. .......... 514/357 |
| 5,750,704 A | 5/1998 | Shiokawa et al. .......... 546/275.1 |
| 5,830,826 A | 11/1998 | Fischer et al. .......... 504/195 |
| 5,847,211 A | 12/1998 | Fischer et al. .......... 564/123 |
| 5,849,768 A | 12/1998 | Minamida et al. .......... 514/357 |
| 5,852,012 A | 12/1998 | Maienfisch et al. .......... 514/229.2 |
| 5,935,981 A | 8/1999 | Minamida et al. .......... 514/365 |
| 5,981,567 A | 11/1999 | Fischer et al. .......... 514/409 |
| 5,994,274 A | 11/1999 | Fischer et al. .......... 504/282 |
| 6,022,871 A | 2/2000 | Maienfisch et al. .......... 514/229.2 |
| 6,022,967 A | 2/2000 | Shiokawa et al. .......... 544/298 |
| 6,110,872 A | 8/2000 | Lieb et al. .......... 504/284 |
| 6,114,374 A | 9/2000 | Lieb et al. .......... 514/424 |
| 6,124,297 A | 9/2000 | Minamida et al. .......... 514/255 |
| 6,133,296 A | 10/2000 | Lieb et al. .......... 514/343 |
| 6,140,358 A | 10/2000 | Lieb et al. .......... 514/425 |
| 6,160,126 A | 12/2000 | Kando et al. .......... 548/477 |
| 6,172,255 B1 | 1/2001 | Fischer et al. .......... 560/24 |
| 6,187,773 B1 | 2/2001 | Wu et al. .......... 514/245 |
| 6,200,932 B1 | 3/2001 | Fischer et al. .......... 504/225 |
| 6,232,309 B1 | 5/2001 | Shiokawa et al. .......... 514/222.5 |
| 6,251,830 B1 | 6/2001 | Fischer et al. .......... 504/251 |
| 6,255,342 B1 | 7/2001 | Lieb et al. .......... 514/533 |
| 6,271,180 B2 | 8/2001 | Lieb et al. .......... 504/292 |
| 6,288,102 B1 | 9/2001 | Hagemann et al. .......... 514/409 |
| 6,297,374 B1 | 10/2001 | Shiokawa et al. .......... 544/55 |
| 6,306,414 B1 * | 10/2001 | Koike .......... 424/405 |
| 6,316,486 B1 | 11/2001 | Lieb et al. .......... 514/411 |
| 6,344,453 B1 | 2/2002 | Shiokawa et al. .......... 514/223.8 |
| 6,358,887 B1 | 3/2002 | Fischer et al. .......... 504/284 |
| 6,359,151 B2 | 3/2002 | Lieb et al. .......... 549/265 |
| 6,376,487 B1 | 4/2002 | Maienfisch et al. .......... 514/229.2 |
| 6,380,246 B1 | 4/2002 | Lieb et al. .......... 514/462 |
| 6,388,123 B1 | 5/2002 | Lieb et al. .......... 560/76 |
| 6,391,912 B1 | 5/2002 | Hagemann et al. .......... 514/444 |
| 6,407,248 B1 | 6/2002 | Minamida et al. .......... 546/331 |
| 6,417,370 B1 | 7/2002 | Lieb et al. .......... 548/408 |
| 6,451,843 B1 | 9/2002 | Lieb et al. .......... 514/422 |
| 6,458,965 B1 | 10/2002 | Lieb et al. .......... 548/408 |
| 6,469,196 B2 | 10/2002 | Fischer et al. .......... 560/105 |
| 6,472,419 B1 | 10/2002 | Fischer et al. .......... 514/425 |
| 6,479,489 B1 | 11/2002 | Fischer et al. .......... 514/235.5 |
| 6,486,343 B1 | 11/2002 | Lieb et al. .......... 560/39 |
| 6,504,036 B1 | 1/2003 | Lieb et al. .......... 549/265 |
| 6,511,942 B1 | 1/2003 | Lieb et al. .......... 504/299 |
| 6,514,954 B1 * | 2/2003 | Senn et al. .......... 514/150 |
| 6,555,567 B1 | 4/2003 | Fischer et al. .......... 514/409 |
| 6,589,976 B1 | 7/2003 | Fischer et al. .......... 514/409 |
| 6,596,873 B1 | 7/2003 | Lieb et al. .......... 546/256 |
| 6,864,276 B2 * | 3/2005 | Fischer et al. .......... 514/409 |
| 2001/0004629 A1 | 6/2001 | Lieb et al. .......... 504/292 |
| 2001/0046994 A1 | 11/2001 | Wu et al. .......... 514/241 |
| 2002/0010204 A1 | 1/2002 | Lieb et al. .......... 514/424 |
| 2002/0022575 A1 | 2/2002 | Fischer et al. .......... 504/221 |
| 2002/0072617 A1 | 6/2002 | Hagemann et al. .......... 548/541 |
| 2002/0161034 A1 | 10/2002 | Hagemann et al. .......... 514/432 |
| 2003/0045432 A1 | 3/2003 | Fischer et al. .......... 504/221 |
| 2003/0073851 A1 | 4/2003 | Lieb et al. .......... 548/366.4 |
| 2003/0096806 A1 | 5/2003 | Lieb et al. .......... 514/212.01 |
| 2003/0144504 A1 | 7/2003 | Fischer et al. .......... 544/54 |

FOREIGN PATENT DOCUMENTS

| | | |
|---|---|---|
| DE | 36 39 877 | 5/1988 |
| DE | 37 12 307 | 10/1988 |
| JP | 63-287764 | 11/1988 |
| JP | 63-307857 | 12/1988 |
| JP | 2-207083 | 8/1990 |
| JP | 3-220176 | 9/1991 |
| JP | 3-246283 | 11/1991 |
| JP | 3-255072 | 11/1991 |

| | | |
|---|---|---|
| JP | 3-279359 | 12/1991 |
| JP | 4-9371 | 1/1992 |
| JP | 5-178833 | 7/1993 |
| JP | 7-173157 | 7/1995 |
| JP | 8-291171 | 11/1996 |
| WO | 91/17659 | 11/1991 |
| WO | 97/36868 | 10/1997 |
| WO | 99/24437 | 5/1999 |
| WO | 99/60857 | 12/1999 |

OTHER PUBLICATIONS

Weeds, 15, (month unavailable) 1967, pp. 20-22, "Calculating Synergistic and Antagonistic Responses of Herbicide Combinations" by S. R. Colby.

Chem. Ind., 37, (month unavailable) 1985, pp. 730-732, "Schiffsfarben—eine Spezialität der seenahen Lackindustrie" by H. R. Ungerer.

* cited by examiner

ACTIVE SUBSTANCE COMBINATIONS HAVING INSECTICIDAL AND ACARICDAL PROPERTIES

This application is a division of U.S. application Ser. No. 10/276,579, filed Nov. 14, 2002, now U.S. Pat. No. 6,864,276, which was filed under 35 U.S.C. 371 as a national stage application of International Application No. PCT/EP01105139, filed May 7, 2001, which was published in German as International Patent Publication WO 01/89300 on Nov. 29, 2001, which is entitled to the right of priority of German Patent Application No. 100 24 934.5, filed May 19, 2000.

The present invention relates to novel active compound combinations comprising known cyclic ketoenols on the one hand and other known insecticidally active compounds on the other hand, which combinations are highly suitable for controlling animal pests such as insects and undesired acarides.

It is already known that certain cyclic ketoenols have herbicidal, insecticidal and acaricidal properties. The activity of these substances is good; however, at low application rates it is sometimes unsatisfactory.

Unsubstituted bicyclic 3-aryl-pyrrolidine-2,4-dione derivatives (EP-A-355 599 and EP-A-415 211) and substituted monocyclic 3-aryl-pyrrolidine-2,4dione derivatives (EP-A-377 893 and EP-A442 077) with herbicidal, insecticidal or acalicidal action are known.

Also known are polycyclic 3-arylpyrrolidine-2,4-dione derivatives (EP-A-442 073) and 1H-arylpyrrolidine-dione derivatives (EP-A-456 063, EP-A-521 334, EP-A-596 298, EP-A-613 884, EP-A-613 885, WO 94/01 997, WO 95/26 954, WO 95/20 572, EP-A-0 668 267, WO 96/25 395, WO 96/35 664, WO 97/01 535, WO 97/02 243, WO 97/36 868, WO 97/43 275, WO 98/05 638, WO 98/06 721, WO 98/25 928, WO 99/16 748, WO 99/24 437, WO 99/43 649, WO 99/48 869 and WO 99/55 673).

Furthermore, it is already known that numerous heterocycles, organotin compounds, benzoylureas and pyrethroids have insecticidal and acaricidal properties (cf. WO 93/22 297, WO 93/10083, DE-A-2 641 343, EP-A-347 488, EP-A-210 487, U.S. Pat. No. 3,364,177 and EP-A-234 045). However, the activity of these substances is not always satisfactory.

It has now been found that mixtures of compounds of the formula (I)

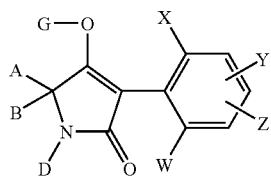

in which
X represents halogen, alkyl, alkoxy, halogenoalkyl, halogenoalkoxy or cyano,
W, Y and Z independently of one another each represent hydrogen, halogen, alkyl, alkoxy, halogenoalkyl, halogenoalkoxy or cyano,
A represents hydrogen, in each case optionally halogen-substituted alkyl, alkoxyalkyl, saturated, optionally substituted cycloalkyl, in which optionally at least one ring atom is replaced by a heteroatom,
B represents hydrogen or alkyl,
A and B together with the carbon atom to which they are attached represent a saturated or unsaturated unsubstituted or substituted cycle which optionally contains at least one heteroatom,
D represents hydrogen or an optionally substituted radical selected from the group consisting of alkyl, alkenyl, alkoxyalkyl, saturated cycloalkyl in which optionally one or more ring members are replaced by heteroatoms,
A and D together with the atoms to which they are attached represent a saturated or unsaturated cycle which is unsubstituted or substituted in the A,D moiety and optionally contains at least one heteroatom,
G represents hydrogen (a) or represents one of the groups

(b)

(c)

(d)

(e)

E or
(f)

(g)

in which
E represents a metal ion or an ammonium ion,
L represents oxygen or sulphur,
M represents oxygen or sulphur,
$R^1$ represents in each case optionally halogen-substituted alkyl, alkenyl, alkoxyalkyl, alkylthioalkyl, polyalkoxyalkyl or optionally halogen-, alkyl- or alkoxy-substituted cycloalkyl which may be interrupted by at least one heteroatom, in each case optionally substituted phenyl, phenylalkyl, hetaryl, phenoxyalkyl or hetaryloxyalkyl,
$R^2$ represents in each case optionally halogen-substituted alky, alkenyl, alkoxyalkyl, polyalkoxyalkyl or represents in each case optionally substituted cycloalkyl, phenyl or benzyl,
$R^3$ represents optionally halogen-substituted alkyl or optionally substituted phenyl,
$R^4$ and $R^5$ independently of one another each represent in each case optionally halogen-substituted alkyl, alkoxy, alkylamino, dialkylamino, alkylthio, alkenylthio, cycloalkylthio or represent in each case optionally substituted phenyl, benzyl, phenoxy or phenylthio and
$R^6$ and $R^7$ independently of one another each represent hydrogen, in each case optionally halogen-substituted alkyl, cycloalkyl, alkenyl, alkoxy, alkoxyalkyl, represent optionally substituted phenyl, represent optionally substituted benzyl or together with the N atom to which they are attached represent an optionally substituted ring which is optionally interrupted by oxygen or sulphur and at least one agonist or antagonist of acetylcholine receptors of the formula (HI) are synergistically active and are suitable for controlling animal pests.

Depending inter alia on the nature of the substituents, the compounds of the formula (I) can be present as geometrical and/or optical isomers or isomer mixtures of varying composition, which, if appropriate, can be separated in a customary manner. The present invention provides both the pure isomers and the isomer mixtures, their preparation and use, and compositions comprising them. Hereinbelow, for the sake of simplicity, only compounds of the formula (I) are referred to, although this means both the pure compounds and, if appropriate, mixtures with varying proportions of isomeric compounds.

The agonists and antagonists of the nicotinic acetylcholine receptors are known compounds which are known from the following publications:

European Published Specifications Nos. 464 830, 428 941, 425 978, 386 565, 383 091, 375 907, 364 844, 315 826, 259 738, 254 859, 235 725, 212 600, 192 060, 163 855, 154 178, 136 636, 136 686, 303 570, 302 833, 306 696, 189 972, 455 000, 135 956, 471 372, 302 389, 428 941, 376 279, 493 369, 580 553, 649 845, 685 477, 483 055,580 553;

German Offenlegungsschriften Nos. 3 639 877, 3 712 307;

Japanese Published Specifications Nos. 03 220 176, 02 207 083, 63 307 857, 63 287 764, 03 246 283, 04 9371, 03 279 359, 03 255 072, 05 178 833, 07 173 157, 08 291 171;

U.S. Pat. Nos. 5,034,524, 4,948,798, 4,918,086, 5,039,686, 5,034,404, 5,532,365;

PCT Applications Nos. WO 91/17 659, 91/4965;

French Application No. 2 611 114;

Brazilian Application No. 88 03 621.

The generic formulae and definitions described in these publications, and also the individual compounds described therein, are expressly incorporated herein by reference.

Some of these compounds are summarized under the term nitromethylenes, nitroimines and related compounds.

Preferably, these compounds can be summarized under the formula (II)

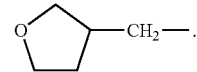

in which
R represents hydrogen or represents optionally substituted radicals selected from the group consisting of acyl, alkyl, aryl, aralkyl, heterocyclyl, heteroaryl and heteroarylalkyl;
A' represents a monofunctional group selected from the group consisting of hydrogen, acyl, alkyl, aryl or represents a bifunctional group which is linked to the radical Z';
E' represents an electron-withdrawing radical;
X' represents the radicals —CH= or =N—, where the radical —CH= may be linked to the radical Z' instead of an H atom;
Z' represents a monofunctional group selected from the group consisting of alkyl, —O—R, —S—R,

where the radicals R are identical or different and are as defined above,
or represents a bifunctional group which is linked to the radical A' or to the radical X'.

Particular preference is given to compounds of the formula (II) in which the radicals have the following meaning:
R represents hydrogen and represents optionally substituted radicals selected from the group consisting of acyl, alkyl, aryl, aralkyl, heterocyclylalkyl, heteroaryl, heteroarylalkyl.

Examples of acyl radicals are formyl, alkylcarbonyl, arylcarbonyl, alkylsulphonyl, arylsulphonyl, (alkyl-)-(aryl-)-phosphoryl, which may themselves be substituted.

Examples of alkyl are $C_1$–$C_{10}$-alkyl, in particular $C_1$–$C_4$-alkyl, specifically methyl, ethyl, i-propyl, sec- or t-butyl, which may themselves be substituted.

Examples of aryl are phenyl, naphthyl, in particular phenyl.

Examples of aralkyl are phenylmethyl, phenethyl.

An example of heterocyclylalkyl is the radical

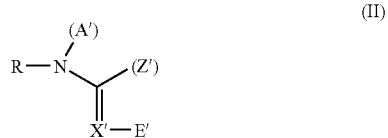

Examples of heteroaryl are heteroaryl having up to 10 ring atoms and N, O, S, in particular N, as heteroatoms. Specific examples are thienyl, furyl, thiazolyl, imidazolyl, pyridyl, benzothiazolyl, pyridazinyl.

Examples of heteroarylalkyl are heteroarylmethyl, heteroarylethyl having up to 6 ring atoms and N, O, S, in particular N, as heteroatoms, in particular optionally substituted heteroaryl as defined under heteroaryl.

Substituents which may be mentioned by way of example and by way of preference are:
alkyl having preferably 1 to 4, in particular 1 or 2, carbon atoms, such as methyl, ethyl, n- and i-propyl and n-, i- and t-butyl; alkoxy having preferably 1 to 4, in particular 1 or 2, carbon atoms, such as methoxy, ethoxy, n- and i-propyloxy and n-, i- and t-butyloxy; alkylthio having preferably 1 to 4, in particular 1 or 2, carbon atoms, such as methylthio, ethylthio, n- and i-propylthio and n-, i- and t-butylthio; halogenoalkyl having preferably 1 to 4, in particular 1 or 2, carbon atoms and preferably 1 to 5, in particular 1 to 3, halogen atoms, the halogen atoms being identical or different, and preferred halogen atoms being fluorine, chlorine or bromine, in particular fluorine, such as trifluoromethyl, hydroxyl; halogen, preferably fluorine, chlorine, bromine and iodine, in particular fluorine, chlorine and bromine, cyano; nitro; amino; monoalkyl- and dialkylamino having preferably 1 to 4, in particular 1 or 2, carbon atoms per alkyl group, such as methylamino, methylethylamino, n- and i-propylamino and methyl-n-butylamino; carboxyl; carbalkoxy having preferably 2 to 4, in particular 2 or 3, carbon atoms, such as carbomethoxy and carboethoxy; sulpho (—$SO_3H$);

alkylsulphonyl having preferably 1 to 4, in particular 1 or 2, carbon atoms, such as methylsulphonyl and ethylsulphonyl; arylsulphonyl having preferably 6 or 10 aryl carbon atoms, such as phenylsulphonyl, and also heteroarylamino and heteroarylalkylamino such as chloropyridylamino and chloropyridylmethylamino.

A' represents hydrogen or represents an optionally substituted radical selected from the group consisting of acyl, alkyl, aryl, which are preferably as defined under R, A' furthermore represents a bifunctional group. Examples include optionally substituted alkylene having 1 to 4, in particular 1 or 2, C atoms, examples of substituents being the substituents which have been listed further above (and where the alkylene groups may be interrupted by heteroatoms from the group consisting of N, O, S).

A' and Z' together with the atoms to which they are attached may form a saturated or unsaturated heterocyclic ring. The heterocyclic ring may contain a further 1 or 2 identical or different heteroatoms and/or hetero groups. Preferred heteroatoms are oxygen, sulphur or nitrogen, and preferred hetero groups are N-alkyl, where the alkyl of the N-alkyl group contains preferably 1 to 4, in particular 1 or 2, carbon atoms. Examples of alkyl include methyl, ethyl, n- and i-propyl, and n-, i- and t-butyl. The heterocyclic ring contains 5 to 7, preferably 5 or 6, ring members.

Examples of compounds of the formula (II) in which A' and Z' together with the atoms to which they are attached form a ring include the following:

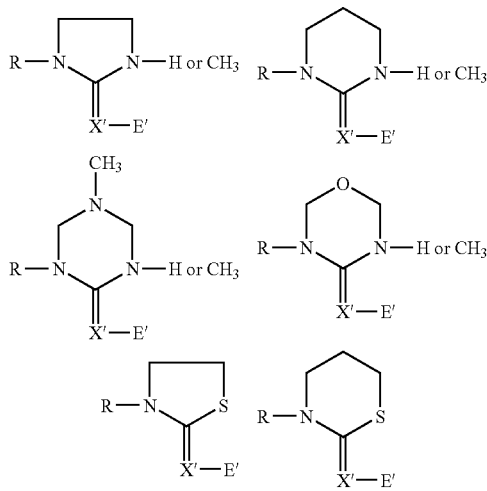

in which
E', R and X' are each as defined above and further below.

E' represents an electron-withdrawing radical, specific examples being NO$_2$, CN, halogenoalkylcarbonyl, such as halogeno-C$_1$–C$_4$-alkylcarbonyl, for example COCF$_3$, alkylsulphonyl (for example SO$_2$—CH$_3$), halogenoalkylsulphonyl (for example SO$_2$CF$_3$) and with particular preference NO$_2$ or CN.

X' represents —CH= or —N=.

Z' represents an optionally substituted radical selected from the group consisting of alkyl, —OR, —SR, —NRR, where R and the substituents are preferably as defined above.

Z' may, in addition to the ring mentioned above, together with the atom to which it is attached and the radical

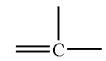

instead of X', form a saturated or unsaturated heterocyclic ring. The heterocyclic ring may contain a further 1 or 2 identical or different heteroatoms and/or hetero groups. Preferred heteroatoms are oxygen, sulphur or nitrogen and preferred hetero groups are N-alkyl, where the alkyl or N-alkyl group contains preferably 1 to 4, preferably 1 or 2, carbon atoms. Examples of alkyl include methyl, ethyl, n- and i-propyl and n-, i- and t-butyl. The heterocyclic ring contains 5 to 7, preferably 5 or 6, ring members. Examples of the heterocyclic ring include pyrrolidine, piperidine, piperazine, hexamethylenimine, morpholine and N-methylpiperazine.

The agonists and antagonists of the nicotinic acetylcholine receptors are particularly preferably compounds of the formula (II) in which R represents

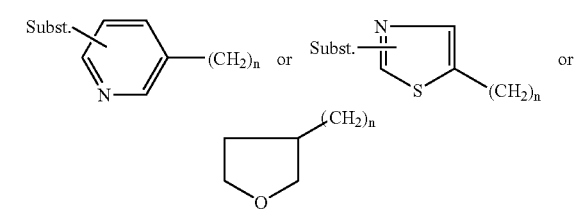

where
n represents 0, 1 or 2, and preferably represents 1,
Subst. represents one of the substituents mentioned above, especially halogen, in particular chlorine, and A', Z', X' and E' are each as defined above.

R represents in particular

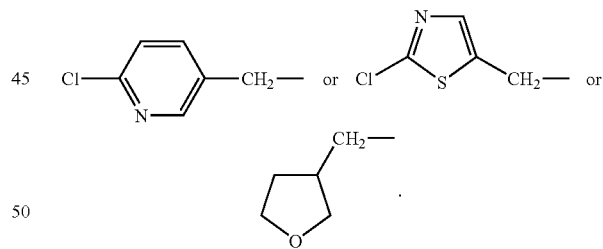

The following compounds are specific examples:

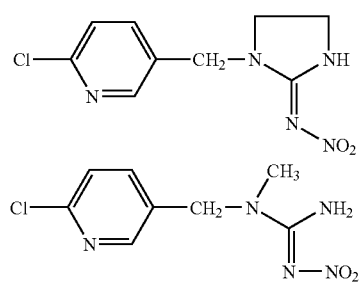

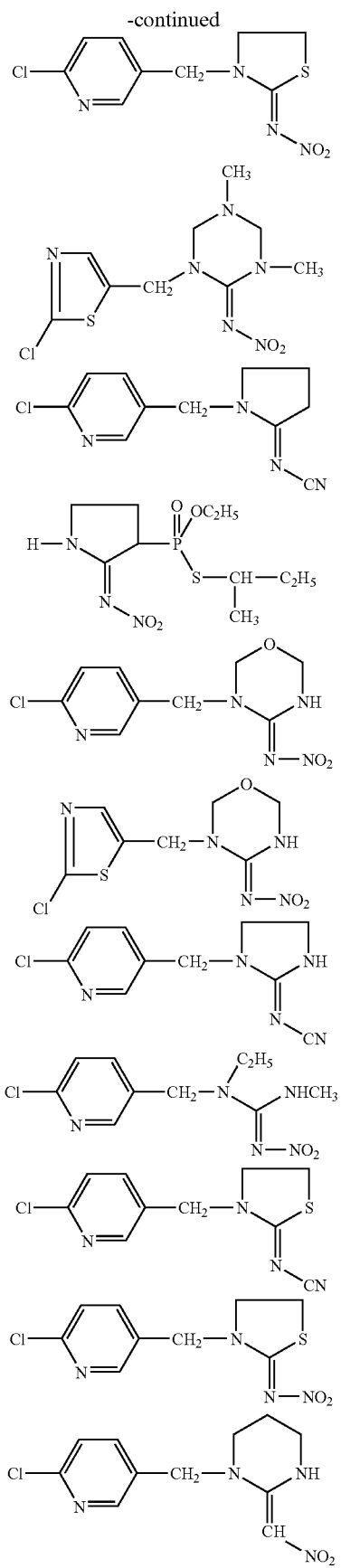
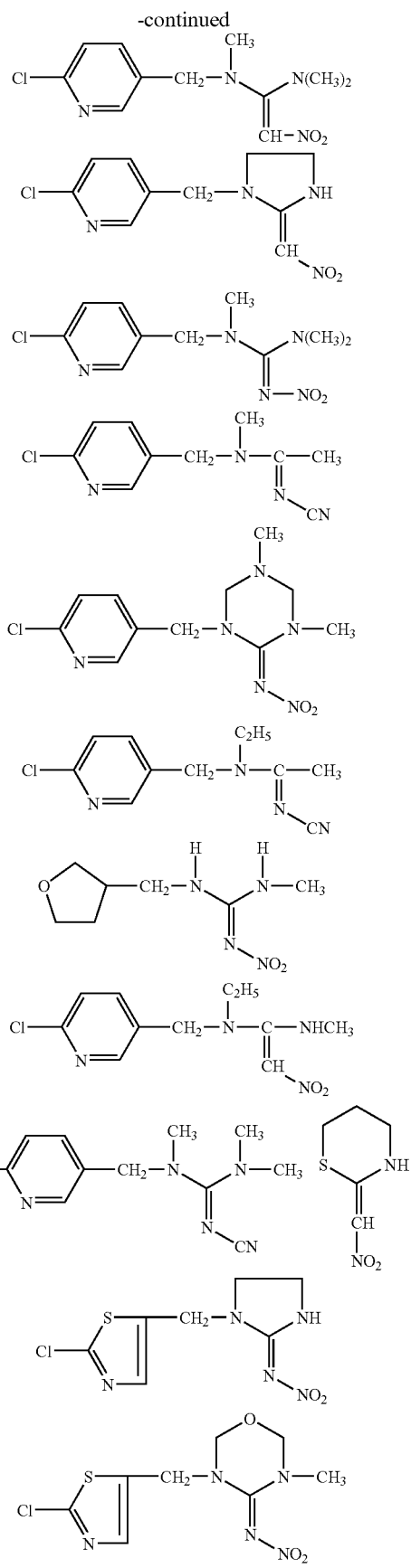

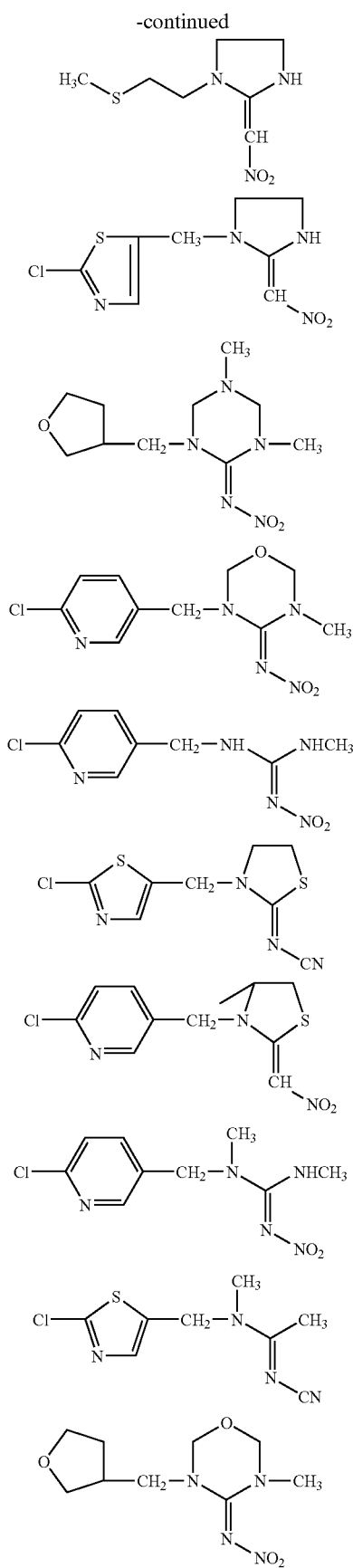
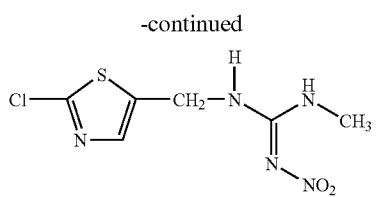
Very particularly preferred agonists and antagonists of the nicotinic acetylcholine receptors are compounds of the following formulae:
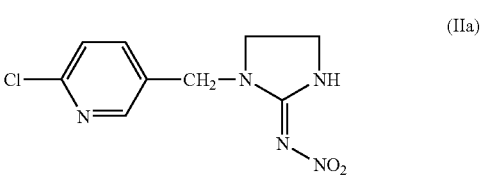
(IIa)
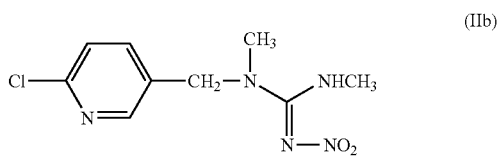
(IIb)
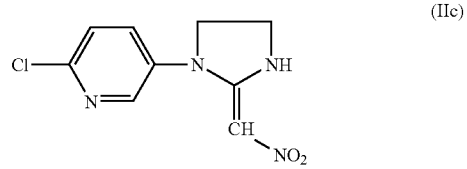
(IIc)
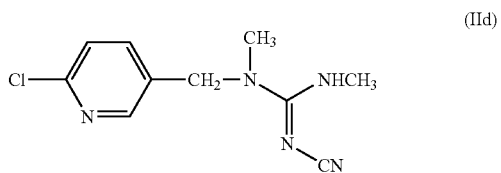
(IId)
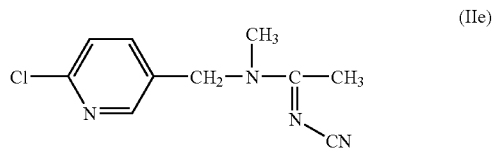
(IIe)
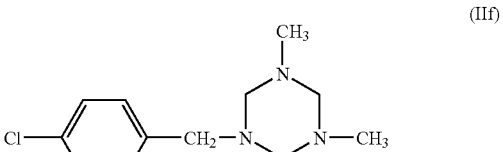
(IIf)
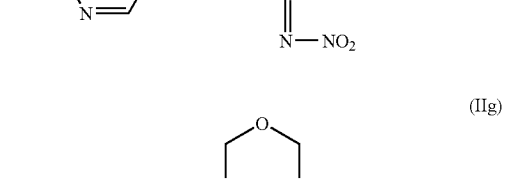
(IIg)

-continued

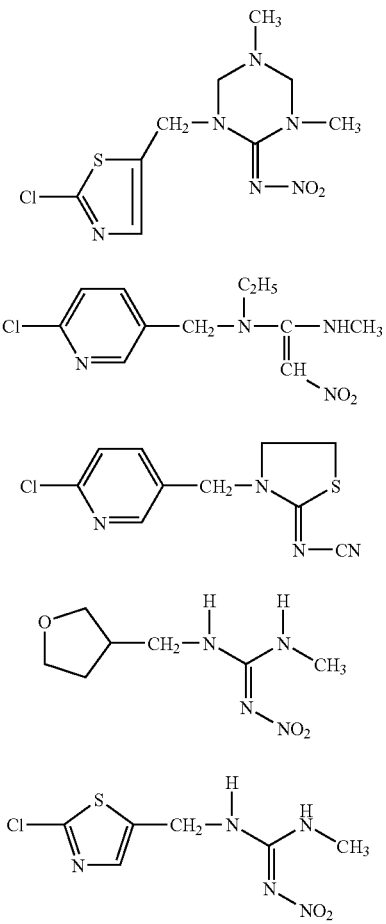

in particular a compound of the following formula

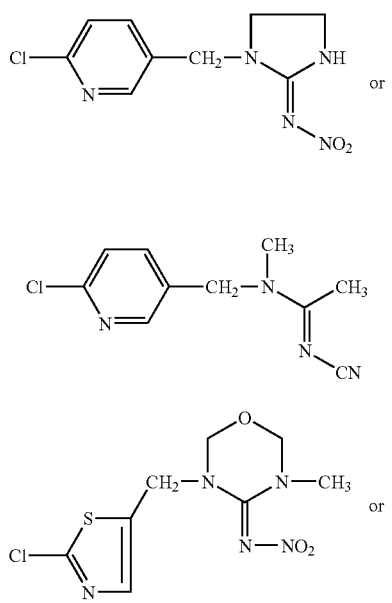

-continued

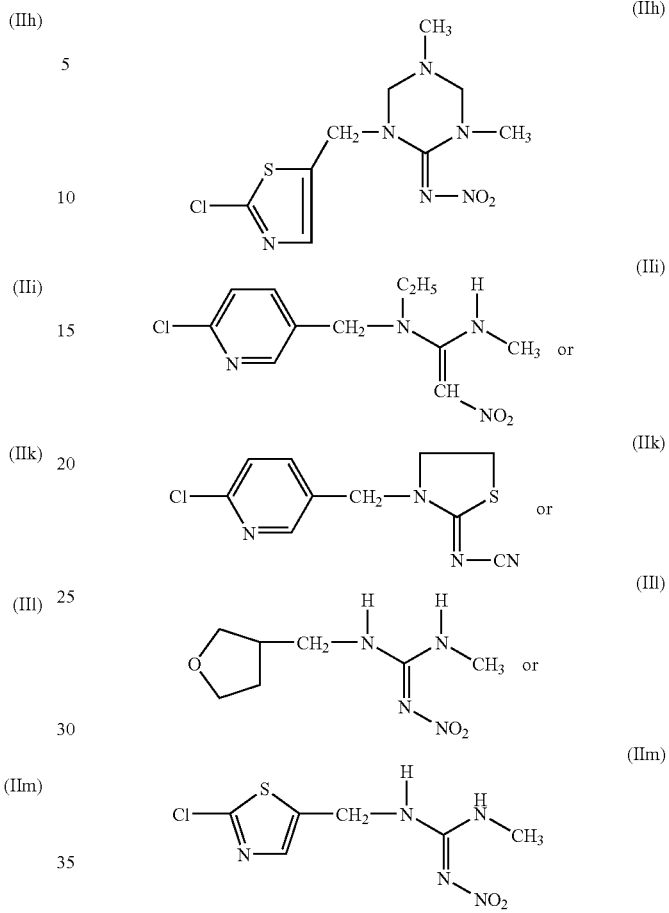

Very particular preference is given to the compounds of the formulae (IIa) and (IIk).

Furthermore, very particular preference is given to the compounds of the formulae (IIe), (IIg), (IIh), (III), (IIc) and (IIm).

Preference is given to active compound combinations comprising compounds of the formula (I) in which the radicals are as defined below:

W preferably represents hydrogen, $C_1$–$C_4$-alkyl, $C_1$–$C_4$-alkoxy, chlorine, bromine or fluorine, X preferably represents $C_1$–$C_4$-alkyl, $C_1$–$C_4$-alkoxy, $C_1$–$C_4$-halogenoalkyl, fluorine, chlorine or bromine, Y and Z independently of one another each preferably represent hydrogen, $C_1$–$C_4$-alkyl, halogen, $C_1$–$C_4$-alkoxy or $C_1$–$C_4$-halogenoalkyl, A preferably represents hydrogen or in each case optionally halogen-substituted $C_1$–$C_6$-alkyl or $C_3$–$C_8$-cycloalkyl, B preferably represents hydrogen, methyl or ethyl, A, B and the carbon atom to which they are attached preferably represent saturated $C_3$–$C_6$-cycloalkyl in which optionally one ring member is replaced by oxygen or sulphur and which is optionally mono- or disubstituted by $C_1$–$C_4$-alkyl, trifluoromethyl or $C_1$–$C_4$-alkoxy, D preferably represents hydrogen, in each case optionally fluorine- or chlorine-substituted $C_1$–$C_6$-alkyl, $C_3$–$C_4$-alkenyl or $C_3$–$C_6$-cycloalkyl, A and D together preferably represent in each case optionally methyl-substituted $C_3$–$C_4$-alkanediyl in which optionally one methylene group is replaced by sulphur.

G preferably represents hydrogen (a) or represents one of the groups

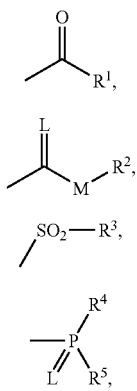

(b)

(c)

(d)

(e)

$E^{(f)}$ and

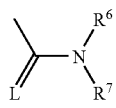

(g)

in particular (a), (b), (c) or (g)

in which

E represents a metal ion or an ammonium ion,

L represents oxygen or sulphur and

M represents oxygen or sulphur, $R^1$ preferably represents in each case optionally halogen-substituted $C_1$–$C_{10}$-alkyl, $C_2$–$C_{10}$-alkenyl, $C_1$–$C_4$-alkoxy-$C_1$–$C_4$-alkyl, $C_1$–$C_4$-alkylthio-$C_1$–$C_4$-alkyl or optionally fluorine-, chlorine-, $C_1$–$C_4$-alkyl- or $C_1$–$C_2$-alkoxy-substituted $C_3$–$C_6$-cycloalkyl, represents optionally fluorine-, chlorine-, bromine-, cyano-, nitro-, $C_1$–$C_4$-alkyl-, $C_1$–$C_4$-alkoxy-, trifluoromethyl- or trifluoromethoxy-substituted phenyl, represents in each case optionally chlorine- or methyl-substituted pyridyl or thienyl, $R^2$ preferably represents in each case optionally fluorine- or chlorine-substituted $C_1$–$C_{10}$-alkyl, $C_2$–$C_{10}$-alkenyl, $C_1$–$C_4$-alkoxy-$C_2$–$C_4$-alkyl, represents optionally methyl- or methoxy-substituted $C_5$–$C_6$-cycloalkyl or represents in each case optionally fluorine-, chlorine-, bromine-, cyano-, nitro-, $C_1$–$C_4$-alkyl-, $C_1$–$C_4$-alkoxy-, trifluoromethyl- or trifluoromethoxy-substituted phenyl or benzyl, $R^3$ preferably represents optionally fluorine-substituted $C_1$–$C_4$-alkyl or represents optionally fluorine-, chlorine-, bromine-, $C_1$–$C_4$-alkyl-, $C_1$–$C_4$-alkoxy-, trifluoromethyl-, trifluoromethoxy-, cyano- or nitro-substituted phenyl, $R^4$ preferably represents in each case optionally fluorine- or chlorine-substituted $C_1$–$C_4$-alkyl, $C_1$–$C_4$-alkoxy, $C_1$–$C_4$-alkylamino, $C_1$–$C_4$-alkylthio or represents in each case optionally fluorine-, chlorine-, bromine-, nitro-, cyano-, $C_1$–$C_4$-alkoxy-, trifluoromethoxy-, $C_1$–$C_4$-alkylthio-, $C_1$–$C_4$-halogenoalkylthio-, $C_1$–$C_4$-alkyl- or trifluoromethyl-substituted phenyl, phenoxy or phenylthio, $R^5$ preferably represents $C_1$–$C_4$-alkoxy or $C_1$–$C_4$-thioalkyl, $R^6$ preferably represents $C_1$–$C_6$-alkyl, $C_3$–$C_6$-cycloalkyl, $C_1$–$C_6$-alkoxy, $C_3$–$C_6$-alkenyl, $C_1$–$C_4$-alkoxy-$C_1$–$C_4$-alkyl, $R^7$ preferably represents $C_1$–$C_6$-alkyl, $C_3$–$C_6$-alkenyl or $C_1$–$C_4$-alkoxy-$C_1$–$C_4$-alkyl, $R^6$ and $R^7$ together preferably represent an optionally methyl- or ethyl-substituted $C_3$–$C_6$-alkylene radical in which optionally one carbon atom is replaced by oxygen or sulphur, W particularly preferably represents hydrogen, methyl, ethyl, chlorine, bromine or methoxy, X particularly preferably represents chlorine, bromine, methyl, ethyl, propyl, i-propyl, methoxy, ethoxy or trifluoromethyl, Y and Z independently of one another each represent hydrogen, fluorine, chlorine, bromine, methyl, ethyl, propyl, i-propyl, trifluoromethyl or methoxy, A particularly preferably represents methyl, ethyl, propyl, i-propyl, butyl, i-butyl, sec-butyl, tert-butyl, cyclopropyl, cyclopentyl or cyclohexyl, B particularly preferably represents hydrogen, methyl or ethyl, A, B and the carbon atom to which they are attached particularly preferably represent saturated $C_6$Cycloalkyl in which optionally one ring member is replaced by oxygen and which is optionally monosubstituted by methyl, ethyl, methoxy, ethoxy, propoxy or butoxy, D particularly preferably represents hydrogen, represents methyl, ethyl, propyl, i-propyl, butyl, i-butyl, allyl, cyclopropyl, cyclopentyl or cyclohexyl, A and D together particularly preferably represent optionally methyl-substituted $C_3$–$C_4$-alkanediyl, G particularly preferably represents hydrogen (a) or represents one of the groups

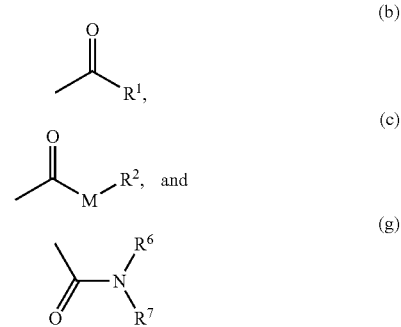

(b)

(c)

and (g)

in which

M represents oxygen or sulphur, $R^1$ particularly preferably represents $C_1$–$C_8$-alkyl, $C_2$–$C_4$-alkenyl, methoxymethyl, ethoxymethyl, ethylthiomethyl, cyclopropyl, cyclopentyl or cyclohexyl, represents optionally fluorine-, chlorine-, bromine-, cyano-, nitro-, methyl-, ethyl-, methoxy-, trifluoromethyl- or trifluoromethoxy-substituted phenyl, represents in each case optionally chlorine- or methyl-substituted pyridyl or thienyl, $R^2$ particularly preferably represents $C_1$–$C_8$-alkyl, $C_2$–$C_4$-alkenyl, methoxyethyl, ethoxyethyl or represents phenyl or benzyl, $R^6$ and $R^7$ independently of one another each particularly preferably represent methyl or ethyl or together represent a $C_5$-alkylene radical in which the $C_3$-methylene group is replaced by oxygen.

W very particularly preferably represents hydrogen or methyl,

X very particularly preferably represents chlorine, bromine or methyl,

Y and Z independently of one another each very particularly preferably represent hydrogen, chlorine, bromine or methyl, A, B and the carbon atom to which they are attached very particularly preferably represent saturated $C_6$-cycloalkyl in which optionally one ring member is replaced by oxygen and which is optionally monosubstituted by methyl, methoxy, ethoxy, propoxy or butoxy, D very particularly preferably represents hydrogen, G very particularly preferably represents hydrogen (a) or represents one of the groups

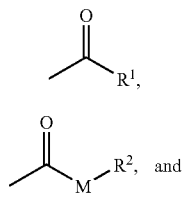

in which

M represents oxygen or sulphur, $R^1$ very particularly preferably represents $C_1$–$C_8$-alkyl, $C_2$–$C_4$-alkenyl, methoxymethyl, ethoxymethyl, ethylmethylthio, cyclopropyl, cyclopentyl, cyclohexyl or represents optionally fluorine-, chlorine-, bromine-, methyl-, methoxy-, trifluoromethyl-, trifluoromethoxy-, cyano- or nitro-substituted phenyl, represents in each case optionally chlorine- or methyl-substituted pyridyl or thienyl, $R^2$ very particularly preferably represents $C_1$–$C_8$-alkyl, $C_2$–$C_4$-alkenyl, methoxyethyl, ethoxyethyl, phenyl or benzyl, $R^6$ and $R^7$ independently of one another each very particularly preferably represent methyl, ethyl or together represent a $C_5$-alkylene radical in which the $C_3$-methylene group is replaced by oxygen.

Particular preference is given to active compound combinations comprising the following compounds of the formula (I)

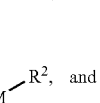

| Example No. | W | X | Y | Z | R | G | m.p. ° C. |
|---|---|---|---|---|---|---|---|
| I-1 | H | Br | 5-CH$_3$ | H | OCH$_3$ | CO—i-C$_3$H$_7$ | 122 |
| I-2 | H | Br | 5-CH$_3$ | H | OCH$_3$ | CO$_2$—C$_2$H$_5$ | 140–142 |
| I-3 | H | CH$_3$ | 5-CH$_3$ | H | OCH$_3$ | H | >220 |
| I-4 | H | CH$_3$ | 5-CH$_3$ | H | OCH$_3$ | CO$_2$—C$_2$H$_5$ | 128 |
| I-5 | CH$_3$ | CH$_3$ | 3-Br | H | OCH$_3$ | H | >220 |
| I-6 | CH$_3$ | CH$_3$ | 3-Cl | H | OCH$_3$ | H | 219 |
| I-7 | H | Br | 4-CH$_3$ | 5-CH$_3$ | OCH$_3$ | CO—i-C$_3$H$_7$ | 217 |
| I-8 | H | CH$_3$ | 4-Cl | 5-CH$_3$ | OCH$_3$ | CO$_2$C$_2$H$_5$ | 162 |
| I-9 | H | CH$_3$ | 4-CH$_3$ | 5-CH$_3$ | OCH$_3$ | CO—N(morpholino) | Oil |
| I-10 | CH$_3$ | CH$_3$ | 3-CH$_3$ | 4-CH$_3$ | OCH$_3$ | H | >220 |
| I-11 | H | CH$_3$ | 5-CH$_3$ | H | OC$_2$H$_5$ | CO—N(morpholino) | Oil |
| I-12 | CH$_3$ | CH$_3$ | 3-Br | H | OC$_2$H$_5$ | CO—i-C$_3$H$_7$ | 212–214 |
| I-13 | H | CH$_3$ | 4-CH$_3$ | 5-CH$_3$ | OC$_2$H$_5$ | CO—n-Pr | 134 |
| I-14 | H | CH$_3$ | 4-CH$_3$ | 5-CH$_3$ | OC$_2$H$_5$ | CO—i-Pr | 108 |
| I-15 | H | CH$_3$ | 4-CH$_3$ | 5-CH$_3$ | OC$_2$H$_5$ | CO—c-Pr | 163 |

The active compound combinations being well tolerated by plants and non-toxic to warm-blooded animals are suitable for controlling animal pests, in particular insects, arachnids and nematodes found in agriculture, in forests, in the protection of stored products and materials and in the hygiene sector. They are preferably used as crop protection agents. They are active against normally sensitive and resistant species, and against all or individual developmental stages. The abovementioned pests include:

From the order of the Isopoda, for example, *Oniscus asellus, Armadillidium vulgare, Porcellio scaber.*

From the order of the Diplopoda, for example, *Blaniulus guttulatus.*

From the order of the Chilopoda, for example, *Geophilus carpophagus, Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp., *Schistocerca gregaria.*

From the order of the Blattaria, for example, *Blatta orientalis, Periplaneta americana, Leucophaea maderae, Blattella germanica.*

From the order of the Dermaptera, for example, *Forficula auricularia.*

From the order of the Isoptera, for example. *Reticulitermes* spp.

From the order of the Phthiraptera, for example, *Pediculus humanus corporis, Haematopinus* spp., *Linognathus* spp., *Trichodectes* spp., *Damalinia* spp.

From the order of the Thysanoptera, for example, *Hercinothrips femoralis, Thrips tabaci, Thrips palmi, Frankliniella occidentalis.*

From the order of the Heteroptera, for example, *Eurygaster* spp., *Dysdercus intermedius, Piesma quadrata, Cimex lectularius, Rhodnius prolixus, Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium comi, Saissetia oleae, Laodelphax striatellus, Nilaparvata lugens, Aonidiella aurantii, Aspidiotus hederae, Pseudococcus* spp., *Psylla* spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pornonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon soistitialis, Costelytra zealandica, Lissorhoptrus oryzophilus.*

From the order of the Hymenoptera, for example, *Diprion* spp., *Hoplocampa* spp., *Lasius* spp., *Monomorium pharaonis, Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp., *Liriomyza* spp.

From the order of the Siphonaptera, for example, *Xenopsylla cheopis, Ceratophyllus* spp.

From the class of the Arachnida, for example, *Scorpio maurus, Latrodectus mactans, Acarus siro, Argas* spp., *Ornithodoros* spp., *Dernanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus* spp.

The plant-parasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *xiphinema* spp., *Trichodorus* spp., *Bursaphelenchus* spp.

According to the invention, it is possible to treat all plants and parts of plants. Plants are to be understood here as meaning all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment according to the invention of the plants and parts of plants with the compounds of the formula (I) alone and in particular with the active compound combinations is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

As already mentioned above, it is possible to treat all plants and their parts according tQ the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering, if appropriate in combination with conventional rmethods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferred and to be treated according to the invention include all plants which, in the genetic modification, received genetic material which imparts particularly advantageous useful traits to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are particularly emphasized are the increased defence of the plants against insects by toxins formed in the plants, in particular those formed by the genetic material from Bacillus thuringiensis (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), Star-Link® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these or still-to-be-developed genetic traits, which plants will be developed and/or marketed in the future.

The plants listed can be treated according to the invention in a particularly advantageous manner with the active compound mixtures according to the invention. The preferred ranges stated above for the mixtures also apply to the treatment of these plants. Particular emphasis is given to the treatment of plants with the mixtures specifically mentioned in the present text.

The ratio of the compounds of the formula (I) and the compounds of the formula (II) used, and the total amount of the mixture, depends on the nature and the occurrence of the insects. For each application, optimum ratios and total amounts used can in each case be determined by test series. In general, the ratio of compounds of the formula (I) to compounds of the formula (II) is from 1:100 to 100:1, preferably from 1:25 to 25:1 and particularly preferably from 1:5 to 5:1. These are parts by weight.

The active compound combinations can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is liquid solvents and/or solid carriers, optionally with the use of surfactants, that is emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are:

for example ammonium salts and ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

The active compound combinations according to the invention can be present in their commercially available formulations and in the use forms, prepared from these formulations, as a mixture with other active compounds, such as insecticides, attractants, sterilants, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Examples of suitable mixing components are the following:

Fungicides:

aldimorph, ampropylfos, ampropylfos potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodi um, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β(2-phenoxyethyl)-1H-1,2,4-triazole-1-ethanol,

α-(2,4-dichlorophenyl)-β-fluoro-β-propyl-1H-1,2,4-triazole-1-ethanol,

α-(2,4-dichlorophenyl)-β-methoxy-α-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxy-phenylacetamide, 1-isopropyl{2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinol, 2',6'-dibromo-2-methyl-4'-trifluoromethoxy-4'-trifluoromethyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulphonyl]-5-(trichloromethyl)-1,3,4-thiadiazole,
2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrole-2,5-dione,
3,5-dichloro-N-[cyano[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulphate,
9H-xanthene-2-[(phenylamino)-carbonyl]-9-carboxylic hydrazide,
bis-(1-methylethyl)-3-methyl-[(3-methylbenzoyl)-oxy]-2,5-thiophenedicarboxylate
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholinehydrochloride,
ethyl[(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(9,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4cyclohexylphenyl)-1,4,5,6-tetrahydro-2-pyrimidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)-acetamide,
N-(6-methoxy-3-pyridinyl)-yclopropanecarboxamide,
N-[2,2,2-trichloro-1-[(chloroacetyl)-amino]-ethyl]-benzamide,
N-[3-chloro-4,5-bis-(2-propinyloxy)-phenyl]-N'-methoxymethanimidamide,
N-formyl-N-hydroxy-DL-alanine-sodium salt,
O,O-diethyl[2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one, Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,

*Bacillus popilliae, Bacillus sphaericus, Bacillus subtilis, Bacillus thuringiensis,* baculoviruses, *Beauveria bassiana, Beauveria tenella,* bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, diflubenzuron, dimethoat, dimethylvinphos, diofenolan, disulfoton, docusat-sodium, dofenapyn, eflusilanate, emamectin, empenthrin, endosulfan, *Entomopfthora* spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, isazofos, isofenphos, isoxathion, ivermectin, nuclear polyhedrosis viruses, lambda-cyhalothrin, lufenuron, malathion, mecarbam, metaldehyde, methamidophos, *Metharhizium anisopliae, Metharhizium flavoviride,* methidathion, methiocarb, methomyl, methoxyfenozide, metolcarb, metoxadiazone, mevinphos, milbemectin, monocrotophos, naled, nitenpyram, nithiazine, novaluron, omethoat, oxamyl, oxydemethon M,

*Paecilomyces fumosoroseus,* parathion A, parathion M, permethrin, phenthoat, phorat, phosalone, phosmet, phosphamidon, phoxim, pirimicarb, pirimiphos A, pirimiphos M, profenofos, promecarb, propoxur, prothiofos, prothoat, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, sulfotep, sulprofos, tau-fluvalinate, tebufenozide, tebufenpyrad, tebupirimphos, teflubenzuron, tefluthrin, temephos, temivinphos, terbufos, tetrachlorvinphos, theta-cypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii* YI 5302
zeta-cyperrnethrin, zolaprofos
(1R-cis)-[5-(phenylmethyl)-3-furanyl]-methyl-3-[(dihydro-2-oxo-3(2H)-furanylidene)-methyl]-2,2-dimethylcyclopropanecarboxylate,
(3-phenoxyphenyl)-methyl-2,2,3,3-tetramethylcyclopropanecarboxylate,
1-[(2-chloro-5-thiazolyl)methyl]tetrahydro-3,5-dimethyl-N-nitro-1,3,5-triazine-2(1H)-imine,
2-(2-chloro-6-fluorophenyl)-4-[4-(1,1-dimethylethyl)phenyl]4,5-dihydro-oxazole,
2-(acetyloxy)-3-dodecyl-1,4-naphthalenedione,
2-chloro-N-[[[4-(1-phenylethoxy)-phenyl]-amino]-carbonyl]-benzamide,
2-chloro-N-[[[4-(2,2-dichloro-1,1-difluoroethoxy)-phenyl]-amino]-carbonyl]-benzamide,
3-methylphenyl propylcarbamate
4-[4-(4-ethoxyphenyl)-4-methylpentyl]-1-fluoro-2-phenoxy-benzene,
4-chloro-2-(1,1-dimethylethyl)-5-[[2-(2,6-dimethyl-4-phenoxyphenoxy)ethyl]thio]-3(2H)-pyridazinone,
4-chloro-2-(2-chloro-2-methylpropyl)-5-[(6-iodo-3-pyridinyl)methoxy]-3(2H)-pyridazinone,
4-chloro-5-[(6-chloro-3-pyridinyl)methoxy]-2-(3,4-dichlorophenyl)-3(2H)-pyridazinone,
*Bacillus thuringiensis* strain EG-2348,
[2-benzoyl-1-(1,1-dimethylethyl)-hydrazinobenzoic acid,
2,2-dimethyl-3-(2,4-dichlorophenyl)-2-oxo-1-oxaspiro[4.5]dec-3-en-4-yl butanoate,
[3-[(6-chloro-3-pyridinyl)methyl]-2-thiazolidinylidene]-cyanamide,
dihydro-2-(nitromethylene)-2H-1,3-thiazine-3(4H)-carboxaldehyde
ethyl [2-[[1,6-dihydro-6-oxo-1-(phenylmethyl)-4-pyridazinyl]oxy]ethyl]-carbamate
N-(3,4,4-trifluoro-1-oxo-3-butenyl)-glycine
N-(4-chlorophenyl)-3-[4-(difluoromethoxy)phenyl]-4,5-dihydro-4-phenyl-1H-pyrazole-1-carboxamide,
N-[(2-chloro-5-thiazolyl)methyl]-N'-methyl-N''-nitroguanidine,
N-methyl-N'-(1-methyl-2-propenyl)-1,2-hydrazinedicarbothioamide,
N-methyl-N'-2-propenyl-1,2-hydrazinedicarbothioamide,
O,O-diethyl[2-(dipropylamino)-2-oxoethyl]-ethylphosphoramidothioate.

Mixtures with other known active compounds such as herbicides or with fertilizers and growth regulators are also possible.

When used as insecticides, the active compound combinations according to the invention can furthermore be present in their commercially available formulations and in the use forms, prepared from these formulations, as a mixture with synergists. Synergists are compounds which increase the action of the active compounds, without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and stored-product pests, the active compound combinations are distinguished by an excellent residual action on wood and clay as well as good stability to alkali on limed substrates.

The active compound combinations according to the invention are not only active against plant pests, hygiene pests and stored-product pests, but also, in the veterinary medicine sector, against animal parasites (ectoparasites) such as hard ticks, soft ticks, mange mites, harvest mites, flies (stinging and licking), parasitizing fly larvae, lice, hair lice, bird lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica, Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyonima* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compound combinations according to the invention are also suitable for controlling arthropods which attack agricultural livestock such as, for example, cattle, sheep, goats, horses, pigs, donkeys, camels, buffaloes, rabbits, chickens, turkeys, ducks, geese, honey-bees, other domestic animals such as, for example, dogs, cats, caged birds, aquarium fish and so-called experimental animals such as, for example, hamsters, guinea pigs, rats and mice. By controlling these arthropods, cases of death and reductions in productivity (for meat, milk, wool, hides, eggs, honey and the like) should be diminished, so that more economical and simpler animal husbandry is possible by the use of the active compound combinations according to the invention.

The active compound combinations according to the invention are used in the veterinary sector in a known manner by enteral administration in the form of, for example, tablets, capsules, potions, drenches, granules, pastes, boluses, the feed-through method, suppositories, by parenteral administration such as, for example, by injections (intramuscularly, subcutaneously, intravenously, intraperitoneally and the like), implants, by nasal administration, by dermal administration in the form of, for example, immersing or dipping, spraying, pouring-on, spotting-on, washing, dusting, and with the aid of active-compound-comprising moulded articles such as collars, ear tags, tail tags, limb bands, halters, marking devices and the like.

When used for cattle, poultry, domestic animals and the like, the active compounds can be applied as formulations (for example powders, emulsions, flowables) comprising the active compounds in an amount of 1 to 80% by weight, either directly or after 100- to 10,000-fold dilution, or they may be used as a chemical dip.

Moreover, it has been found that the active compound combinations according to the invention show a potent insecticidal action against insects which destroy industrial materials.

The following insects may be mentioned by way of example and with preference, but not by way of limitation:

Beetles such as

Hylotrupes bajulus, Chlorophorus pilosis, Anobium punctatum, Xestobium rufovillosum, Ptilinus pecticomis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus spec., Tryptodendronspec., Apate monachus, Bostrychus capucins, Heterobostrychus brunneus, Sinoxylon spec., Dinoderus minutus.

Dermapterans such as

Sirex juvencus, Urocerus gigas, Urocerus gigas taignus, Urocerus augur.

Termnites such as

Kalotermes flavicollis, Cryptotermes brevis, Heterotermes indicola, Reticulitermes flavipes, Reticulitermes santonensis, Reticulitermes lucifugus, Mastotermes darwiniensis, Zooternopsis nevadensis, Coptotermes formosanus.

Bristle-tails such as Lepisma saccharina.

Industrial materials in the present context are understood as meaning non-living materials such as, preferably, polymers, adhesives, glues, paper and board, leather, wood, timber products and paints.

The material which is to be protected from insect attack is very particularly preferably wood and timber products.

Wood and timber products which can be protected by the composition according to the invention, or mixtures comprising it, are to be understood as meaning, for example:

Construction timber, wooden beams, railway sleepers, bridge components, jetties, vehicles made of wood, boxes, pallets, containers, telephone poles, wood lagging, windows and doors made of wood, plywood, chipboard, joinery, or timber products which quite generally are used in house construction or building joinery.

The active compound combinations can be used as such, in the form of concentrates or generally customary formulations such as powders, granules, solutions, suspensions, emulsions or pastes.

The abovementioned formulations can be prepared in a manner known per se, for example by mixing the active compounds with at least one solvent or diluent, emulsifier, dispersant and/or binder or fixative, water repellant, if desired desiccants and UV stabilizers, and if desired colorants and pigments and other processing auxiliaries.

The insecticidal compositions or concentrates used for protecting wood and timber products comprise the active compound according to the invention in a concentration of 0.0001 to 95% by weight, in particular 0.001 to 60% by weight.

The amount of composition or concentrate employed depends on the species and the abundance of the insects and on the medium. The optimal quantity to be employed can be determined in each case by test series upon application. In general, however, it will suffice to employ 0.0001 to 20% by weight, preferably 0.001 to 10% by weight, of the active compound, based on the material to be protected.

A suitable solvent and/or diluent is an organochemical solvent or solvent mixture and/or an oily or oil-type organochemical solvent or solvent mixture of low volatility and/or a polar organochemical solvent or solvent mixture and/or water and, if appropriate, an emulsifier and/or wetter.

Organochemical solvents which are preferably employed are oily or oil-type solvents with an evaporation number of above 35 and a flash point of above 30° C., preferably above 45° C. Such oily and oil-type solvents which are insoluble in water and of low volatility and which are used are suitable mineral oils or their aromatic fractions or mineral-oil-containing solvent mixtures, preferably white spirit, petroleum and/or alkylbenzene.

Mineral oils with a boiling range of 170 to 220° C., white spirit with a boiling range of 170 to 220° C., spindle oil with a boiling range of 250 to 350° C., petroleum and aromatics with a boiling range of 160 to 280° C., oil of terpentine, and the like are advantageously used.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene are used.

The organic oily or oil-type solvents of low volatility and with an evaporation number of above 35 and a flash point of above 30° C., preferably above 45° C., can be replaced in part by organochemical solvents of high or medium volatility, with the proviso that the solvent mixture also has an evaporation number of above 35 and a flash point of above 30° C., preferably above 45° C., and that the insecticide-fungicide mixture is soluble or emulsifiable in this solvent mixture.

In a preferred embodiment, some of the organochemical solvent or solvent mixture is replaced by an aliphatic polar organochemical solvent or solvent mixture. Aliphatic organochemical solvents which contain hydroxyl and/or ester and/or ether groups are preferably used, such as, for example, glycol ethers, esters or the like.

Organochemical binders used for the purposes of the present invention are the synthetic resins and/or binding drying oils which are known per se and which can be diluted in water and/or dissolved or dispersed or emulsified in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin such as indene/coumarone resin, silicone resin, drying vegetable and/or drying oils and/or physically drying binders based on a natural and/or synthetic resin.

The synthetic resin employed as binder can be employed in the form of an emulsion, dispersion or solution. Bitumen or bituminous substances may also be used as binders, in amounts of up to 10% by weight. In addition, colorants, pigments, water repellants, odour-masking agents, and inhibitors or anticorrosive agents and the like, all of which are known per se, can be employed.

In accordance with the invention, the composition or the concentrate preferably comprises, as organochemical binders, at least one alkyd resin or modified alkyd resin and/or a drying vegetable oil. Alkyd resins which are preferably used in accordance with the invention are those with an oil content of over 45% by weight, preferably 50 to 68% by weight.

Some or all of the abovementioned binder can be replaced by a fixative (mixture) or plasticizer (mixture). These additives are intended to prevent volatilization of the active compounds, and also crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, phosphoric esters such as tributyl phosphate, adipic esters such as di-(2-ethylhexyl)-adipate, stearates such as butyl stearate or amyl stearate, oleates such as butyl oleate, glycerol ethers or higher-molecular-weight glycol ethers, glycerol esters and p-toluenesulphonic esters.

Fixatives are based chemically on polyvinyl alkyl ethers such as, for example, polyvinyl methyl ether, or ketones such as benzophenone and ethylenebenzophenone.

Other suitable solvents or diluents are, in particular, water, if appropriate as a mixture with one or more of the abovementioned organochemical solvents or diluents, emulsifiers and dispersants.

Particularly effective timber protection is achieved by industrial-scale impregnating processes, for example the vacuum, double-vacuum or pressure processes.

The ready-to-use compositions may if appropriate also contain other insecticides and if appropriate one or more additional fungicides.

The active compound combinations according to the invention can at the same time be employed for protecting objects which come into contact with saltwater or brackish water, such as hulls, screens, nets, buildings, moorings and signalling systems, against fouling.

Fouling by sessile *Oligochaeta*, such as *Serpulidae*, and by shells and species from the *Ledamorpha* group (goose barnacles), such as various *Lepas* and *Scalpellum* species, or by species from the *Balanomorpha* group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile *Entomostraka* groups, which come under the generic term *Cirripedia* (cirriped crustaceans), is of particular importance.

Surprisingly, it has now been found that the active compound combinations according to the invention have an outstanding antifouling action.

Using the active compound combinations according to the invention, allows the use of heavy metals such as, for example, in bis(trialkyltin) sulphides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl-(bispyridine)-bismuth chloride, tri-n-butyl-tin fluoride, manganese ethylenebisthiocarbamate, zinc dimethyldithiocarbamate, zinc ethylenebisthiocarbamate, zinc salts and copper salts of 2-pyridinethiol 1-oxide, bisdimethyldithiocarbamoylzinc ethylene-bisthiocarbamate, zinc oxide, copper(I) ethylene-bisdithiocarbamate, copper thiocyanate, copper naphthenate and tributyltin halides to be dispensed with, or the concentration of these compounds substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:
algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;

fungicides such as benzo[b]thiophenecarboxylic acid cyclohexylamide S,S-dioxide, dichlofluanid, fluorfolpet, 3-iodo-2-propinyl butylcarbamate, tolylfluanid and azoles such as azaconazole, cyproconazole, epoxyconazole, hexaconazole, metconazole, propiconazole and tebuconazole;

molluscicides such as fentin acetate, metaldehyde, methiocarb, niclosamide, thiodicarb and trimethacarb; or conventional antifouling active compounds such as 4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleiimide.

The antifouling compositions used comprise the active compound in a concentration of 0.001 to 50% by weight, in particular 0.01 to 20% by weight.

Moreover, the antifouling compositions comprise the customary components such as, for example, those described in Ungerer, *Chem. Ind.* 1985, 37, 730–732 and Williams, Antifouling Marine Coatings, Noyes, Park Ridge, 1973.

Besides the algicidal, fungicidal, molluscicidal active compounds and insecticidal active compounds, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The active compound combinations according to the invention may also be incorporated into self-polishing antifouling systems.

The active compound combinations according to the invention are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Aviculariidae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scader.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticuliterrmes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipieins, Culex tarsalis, Drosophila* spp., *Fannia*

From the order of the Lepidoptera, for example, *Achroia grisella, Galleria mellonelia, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Phthirus pubis.*

From the order of the Heteroptera, for example, *Cimex hemipterus, Cimex lectularius, Rhodinus prolixus, Triatoma infestans.*

In the sector of household insecticides, the active compounds can also be used in combination with other suitable active compounds such as phosphoric esters, carbamates, pyrethroids, growth regulators or active compounds from other known classes of insecticides.

They are used as aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

When using the active compound combinations according to the invention, the application rates can be varied within a relatively wide range, depending on the type of application. In the treatment of parts of plants, the application rates of active compounds are generally between 0.1 and 10 000 g/ha, preferably between 10 and 1 000 g/ha.

The good insecticidal and acaricidal action of the active compound combinations according to the invention can be seen from the examples which follow. While the individual active compounds show weaknesses in their action, the combinations show an action which exceeds a simple sum of actions.

A synergistic effect in insecticides and acaricides is always present when the action of the active compound combinations exceeds the total of the actions of the active compounds when applied individually.

The expected action for a given combination of two active compounds can be calculated as follows, using the formula of S. R. Colby, Weeds 15 (1967), 20–22:

If

X is the kill rate when employing active compound A at an application rate of m g/ha or in a concentration of m ppm, Y is the kill rate when employing active compound B at an application rate of n g/ha or in a concentration of n ppm and E is the kill rate when employing active compounds A and B at application rates of m and n g/ha or in a concentration of m and n ppm, then $$E = X + Y - \frac{X \cdot Y}{100}$$

Here, the kill rate is determined in %. 0% means a kill rate which corresponds to that of the control, whereas a kill rate of 100% means that no infestation is observed.

If the actual effect exceeds the calculated value, the action of the combination is superadditive, i.e. a synergistic effect is present. In this case, the actually observed kill rate must exceed the value calculated using the above formula for the expected kill rate (E).

EXAMPLE A

Aphis Gossypii Test

Solvent: 3 parts by weight of dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with water to the desired concentrations.

Cotton leaves (*Gossypium hirsutum*) which are heavily infested by the cotton aphid (*Aphis gossypii*) are treated by being dipped into the preparation of active compound of the desired concentration.

After the desired period of time, the kill in % is determined. 100% means that all aphids have been killed; 0% means that none of the aphids have been killed. The kill rates that are determined are calculated using Colby's formula.

In this test, for example, the following active compound combination according to the present application exhibits a synergistically enhanced activity compared to the active compounds applied individually:

TABLE A

Sheet 1
Plant-damaging insects
*Aphis gossypii* test

| Active compounds | Active compound concentration in ppm | Kill rate in % after $6^d$ | |
|---|---|---|---|
| Ex. I-10 Known | 1.6 | 0 | |
| Ex. II-a known | 1.6 | 25 | |
| Ex. I-10 + Ex. II-a (1:1) according to the invention | 1.6 + 1.6 | found* 95 | Calc.** 25 |

*found = activity found
**calc. = activity calculated using Colby's formula

TABLE A

Sheet 2
Plant-damaging insects
*Aphis gossypii* test

| Active compounds | Active compound concentration in ppm | Kill rate in % after $1^d$ | |
|---|---|---|---|
| Ex. I-10 known | 8 | 0 | |
| Ex. II-g known | 8 | 70 | |
| Ex. I-10 + Ex. II-g (1:1) according to the invention | 8 + 8 | found* 95 | calc.** 70 |

*found = activity found
**calc. = activity calculated using Colby's formula

EXAMPLE B

Myzus Test

Solvent: 3 parts by weight of dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with water to the desired concentrations.

Cabbage leaves (*Brassica oleracea*) which are heavily infested by the peach aphid (*Myzus persicae*) are treated by being dipped into the preparation of active compound of the desired concentration.

After the desired period of time, the kill in % is determined. 100% means that all animals have been killed; 0% means that none of the animals have been killed. The kill rates determined are calculated using Colby's formula.

In this test, for example, the following active compound combination according to the present application exhibits a synergistically enhanced activity compared to the active compounds applied individually:

TABLE B

Sheet 1
Plant-damaging insects
*Myzus* test

| Active compounds | Active compound concentration in ppm | Kill rate in % after $6^d$ | |
|---|---|---|---|
| Ex. I-10 known | 1.6 | 5 | |
| Ex. II-k known | 1.6 | 10 | |
| Ex. I-10 + Ex. II-k (1:1) according to the invention | 1.6 + 1.6 | found* 80 | Calc.** 14.5 |

*found = activity found
**calc. = activity calculated using Colby's formula

TABLE B

Sheet 2
Plant-damaging insects
*Myzus* test

| Active compounds | Active compound concentration in ppm | Kill rate in % after $6^d$ | |
|---|---|---|---|
| Ex. I-10 known | 1.6 | 0 | |
| Ex. II-g known | 1.6 | 10 | |
| Ex. I-10 + Ex. II-g (1:1) according to the invention | 1.6 + 1.6 | found* 95 | Calc.** 10 |

*found = activity found
**calc. = activity calculated using Colby's formula

TABLE B

Sheet 3
Plant-damaging insects
*Myzus* test

| Active compounds | Active compound concentration in ppm | Kill rate in % after $1^d$ | |
|---|---|---|---|
| Ex. I-10 known | 1.6 | 0 | |
| Ex. II-m known | 1.6 | 15 | |
| Ex. I-10 + Ex. II-m (1:1) according to the invention | 1.6 + 1.6 | found* 45 | calc.** 15 |

*found = activity found
**calc. = activity calculated using Colby's formula

EXAMPLE C

Critical Concentration Test/Soil Insects—Treatment of Transgenic Plants

Test insect: *Diabrotica balteata*—larvae in soil

Solvent: 7 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

The preparation of active compound is poured on to the soil. Here, the concentration of active compound in the preparation is virtually irrelevant, only the amount by weight of active compound per volume unit of soil, which is stated in ppm (mg/l), matters. The soil is filled into 0.25 l pots and these are allowed to stand at 20° C.

Immediately after preparation, 5 pre-germinated maize corns of the variety YIELD GUARD (trade mark of Monsanto Comp., USA) are placed into each pot. After 2 days, the test insects are placed into the treated soil. After a further 7 days, the efficacy of the active compound is determined by counting the maize plants that have emerged (1 plant=20% efficacy).

EXAMPLE D

Heliothis Virescens Test—Treatment of Transgenic Plants
Solvent: 7 parts by weight of acetone
Emulsifier: 1 part by weight of alkylaryl polyglycol ether
To produce a suitable preparation of active compound, 1 part by weight of active compound is mixed with the stated amount of solvent and the stated amount of emulsifier, and the concentrate is diluted with water to the desired concentration.

Soya bean shoots (*Glycine max*) of the variety Roundup Ready (trade mark of Monsanto Comp. USA) are treated by being dipped into the preparation of active compound of the desired concentration and are populated with the tobacco budworm Heliothis virescens while the leaves are still moist.

After the desired period of time, the kill of the insects is determined.

What is claimed is:
1. A composition comprising a synergistically effective mixture of
(a) a compound of the formula (I)

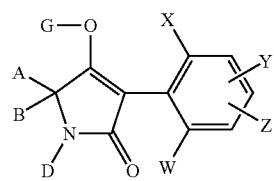

in which
W represents hydrogen or methyl,
X represents chlorine, bromine, or methyl,
Y and Z independently of one another each represent hydrogen, chlorine, bromine, or methyl,
A and B together with the carbon atom to which they are attached represent saturated $C_6$-cycloalkyl in which optionally one ring member is replaced by oxygen and that is optionally monosubstituted by methyl, methoxy, ethoxy, propoxy, or butoxy,
D represents hydrogen,
G represents hydrogen (a) or represents one of the groups

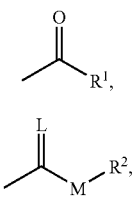

-continued

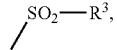

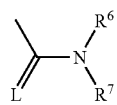

in which
M represents oxygen or sulphur,
$R^1$ represents $C^1$–$C^8$-alkyl, $C^2$–$C^4$-alkenyl, methoxymethyl, ethoxymethyl, ethylmethylthio, cyclopropyl, cyclopentyl, or cyclohexyl, represents optionally fluorine-, chlorine-, bromine-, methyl-, methoxy-, trifluoromethyl-, trifluoromethoxy-, cyano-, or nitro-substituted phenyl, or represents in each case optionally chlorine- or methyl-substituted pyridyl or thienyl,
$R^2$ represents $C^1$–$C^8$-alkyl, $C^2$–$C^4$-alkenyl, methoxyethyl, ethoxyethyl, phenyl, or benzyl,
$R^6$ and $R^7$ independently of one another each represent methyl or ethyl, or $R^6$ and $R^7$ together with the nitrogen to which they are attached represent

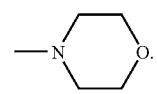

and
(b) at least one agonist or antagonist of nicotinic acetylcholine receptors selected from the group consisting of

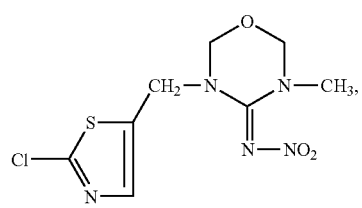

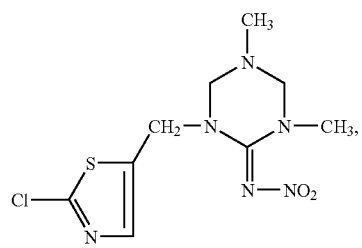

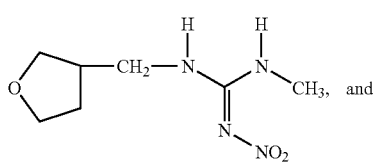 (III)

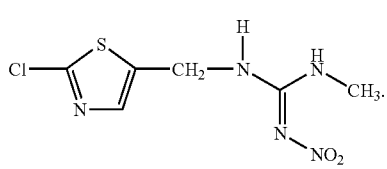 (IIm)

2. A composition according to claim 1, wherein for a compound of the formula (I),

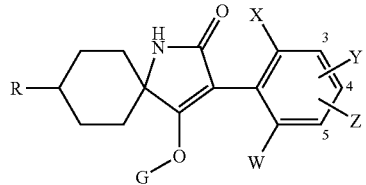 (I)

(1) W is H, X is Br, Y is 5-CH$_3$, Z is H, R is OCH$_3$, and G is CO is CO-i-C$_3$H$_7$;
(2) W is H, X is Br, Y is 5-CH$_3$, Z is H, R is OCH$_3$, and G is CO$_2$—C$_2$H$_5$;
(3) W is H, X is CH$_3$, Y is 5-CH$_3$, Z is H, R is OCH$_3$, and G is H;
(4) W is H, X is CH$_3$, Y is 5-CH$^3$, Z is H, R is OCH$^3$, and G is CO$_2$—C$_2$H$_5$;
(5) W is CH$_3$, X is CH$_3$, Y is 3-Br, Z is H, R is OCH$_3$, and G is H;
(6) W is CH$_3$, X is CH$_3$, Y is 3-Cl, Z is H, R is OCH$_3$, and G is H;
(7) W is H, X is Br, Y is 4-CH$_3$, Z is 5-CH$_3$, R is OCH$_3$, and G is CO-i-C$_3$H$_7$;
(8) W is H, X is CH$_3$, Y is 4-Cl, Z is 5-CH$_3$, R is OCH$_3$, and G is CO$_2$—C$_2$H$_5$;
(9) W is H, X is CH$_3$, Y is 4-CH$_3$, Z is 5-CH$_3$, R is OCH$_3$, and G is

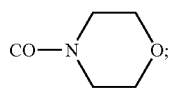

(10) W is CH$_3$, X is CH$_3$, Y is 3-CH$_3$, Z is 4-CH$_3$, R is OCH$_3$, and G is H;
(11) W is H, X is CH$_3$, Y is 5-CH$_3$, Z is H, R is OC$_2$H$_5$, and G is

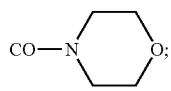

(12) W is CH$_3$, X is CH$_3$, Y is 3-Br, Z is H, R is OC$_2$H$_5$, and G is CO-i-C$_3$H$_7$;

(13) W is H, X is CH$_3$, Y is 4-CH$_3$, Z is 5-CH$_3$, R is OC$_2$H$_5$, and G is CO-n-Pr;
(14) W is H, X is CH$_3$, Y is 4-CH$_3$, Z is 5-CH$_3$, R is OC$_2$H$_5$, and G is CO-i-Pr; or
(15) W is H, X is CH$_3$, Y is 4-CH$_3$, Z is 5-CH$_3$, R is OC$_2$H$_5$, and G is CO-cyclopropyl.

3. A composition according to claim 2 comprising a mixture of
(a) the compound of formula (I) in which W is H, X is CH$_3$, Y is 5-CH$_3$, Z is H, R is OCH$_3$, and G is CO$_2$—C$_2$H$_5$, and
(b) at least one agonist or antagonist of nicotinic acetylcholine receptors selected from the group consisting of

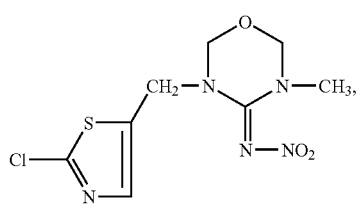 (IIg)

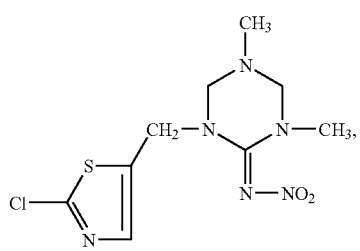 (IIh)

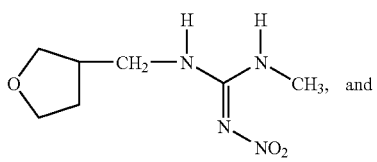 (III)

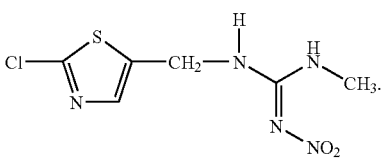 (IIm)

4. A composition according to claim 1 comprising a compound of the formula (I) and the agonist or antagonist of nicotinic acetylcholine receptors of component (b) in a parts-by-weight ratio of from 1:100 to 100:1.

5. A method of controlling insects, arachnids, or nematodes comprising exposing insects, arachnids, or nematodes to a synergistically effective mixture comprising the composition according to claim 1.

6. A process for preparing pesticides comprising mixing a synergistically effective mixture comprising the composition according to claim 1 with extenders and/or surfactants.

* * * * *